(12) United States Patent
Passaro et al.

(10) Patent No.: US 7,129,364 B2
(45) Date of Patent: Oct. 31, 2006

(54) PROCESS FOR THE PREPARATION OF 2-FURYL-N-PENTYLKETONE AND LONGER CHAIN ANALOGS

(75) Inventors: Linda C. Passaro, Alexandria, VA (US); Steven K. Pollack, Silver Spring, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 55 days.

(21) Appl. No.: 10/979,842

(22) Filed: Nov. 2, 2004

(65) Prior Publication Data

US 2006/0094888 A1    May 4, 2006

(51) Int. Cl.
*C07D 307/02* (2006.01)
(52) U.S. Cl. ..................................... 549/483
(58) Field of Classification Search ................ 549/483
See application file for complete search history.

(56) References Cited

U.S. PATENT DOCUMENTS 4,254,043 A    3/1981   Kuta
5,259,701 A    11/1993  Gerhart et al.

OTHER PUBLICATIONS

Medarde et al, Eur. J. Med. Chem., vol. 33, p. 71-77 (1998).*
Corey et al, "Oxidative Hydrolysis of 1,3-Dithiane Derivatives to Carbonyl Compounds Using N-Halosuccinimide Reagents", Journal of Organic Chemistry, vol. 36, No. 23, pp. 3553-3560, 1971.
Gilman et al, "Super-Aromatic Properties of Furan II the Friedel-Crafts Reaction", Chemical Laboratory of Iowa State College, pp. 4197-4205, Oct. 1933.
Gooben et al, "Palladium-Catalyzed Synthesis of Aryl Ketones from Boronic Acids and Carboxylic Acids Activated in Situ by Pivalic Anhydride", European Journal of Organic Chemistry, pp. 3254-3267, 2002.
Gooben et al, "Palladium-Catalyzed Synthesis of Aryl Ketones from Boronic Acids and Carboxylic Acids or Anhydrides", Angwe. Chem. Int. Ed., vol. 40, No. 18, pp. 3458-3460, 2001.
Jun et al, "Hydroacylation of 1-Alkene with Heteroaromatic Aldehyde by Rh(I) and Additives", Tetrahedron Letters, vol. 38, No. 38, pp. 6673-6676, 1997.
Kobayashi et al, "Catalytic Friedel-Crafts Acylation of Heteroaromatics", Topics in Catalysis, vol. 19, No. 1, pp. 43-47, Mar. 2002.
Passaro et al, "Synthesis of 2-Furyl-n-Pentylketone, Antifouling Agent of the Future", Poster Presentation ACS National Meeting Anaheim, CA, Mar. 31, 2004.

* cited by examiner

*Primary Examiner*—Bernard Dentz
(74) *Attorney, Agent, or Firm*—John J. Karasek; Joseph T. Grunkemeyer

(57) ABSTRACT

A process of making furfural-derived ketones is disclosed. These compounds may be useful as marine antifouling agents. The process uses the steps of: reacting a furfural with 1,3-dithiopropane to form a 1,3-dithiane derivative; metalizing the 1,3-dithiane derivative to form a metalodithiane derivative; reacting the metalodithiane derivative with a halide or pseudohalide to form a ketone precursor; and hydrolyzing the ketone precursor to form a furyl ketone.

17 Claims, No Drawings

PROCESS FOR THE PREPARATION OF 2-FURYL-N-PENTYLKETONE AND LONGER CHAIN ANALOGS

BACKGROUND OF THE INVENTION

1. Field of the Invention

The invention relates to a process for the synthesis of 2-furylketones.

2. Description of the Prior Art

Biological fouling, or biofouling, is defined as the unwanted buildup of microorganisms, plants, and animals on artificial surfaces. Marine biofouling is the undesirable accumulation of organisms on any artificial surface that is submerged in seawater, such as ship hulls, seaside piers, sea defenses, or any other surface that is continuously in contact with seawater. Fouling can occur in two basic forms, hard fouling, such as barnacles, and soft fouling, such as grasses and algae.

Current antifoulant technologies have been found to be both harmful to marine life and to the environment. Presently, the most commonly used antifouling agents in marine coatings worldwide are organotin compounds, specifically tri-butyltin oxide (TBTO).

While tri-butyltin agents have been very effective in preventing fouling they also are associated with a vast number of environmental problems, due to their persistence in the environment, such as bioaccumulation, acute toxicity, and reduced reproductive capability of marine organisms. Similar concerns exist for coatings that release copper into the environment.

Naturally occurring antifoulant compounds, those expressed by marine organisms, are only available in limited amounts and often their structural complexity makes synthetic production in large quantities difficult. One analog of a naturally occurring antimicrobial agent, 2-furyl-n-pentylketone, has been a popular synthetic target. Furan derivatives are known to possess marine antifouling properties as disclosed in U.S. Pat. No. 5,259,701 to Gerhart. The majority of past synthetic strategies have involved Friedel-Crafts acylation chemistry and often resulted in poor yields and were rarely applied to large-scale preparations and/or involved the use of complex, expensive reagents. Other oxidative strategies of an α-hydroxyl furan have proven difficult to carry out and the resulting ketone products often require chromatographic purification, which is troublesome for larger scale preparations. Various types of Friedel-Crafts acylation methods have been used to prepare. Most have employed furan and an acid chloride or anhydride with a range of acid catalysts. Other groups have prepared 2-furyl-n-pentylketone by way of a facilitated acylation reaction between boronic acids and anhydrides in the presence of a palladium catalyst. Alternative methods employed to prepare 2-furyl-n-pentylketone have involved an alkylation scheme usually involving either an acid chloride or furfural with the appropriate Grignard reagent. Alkylation in the case of furfural then required oxidation to afford the desired ketone product. Alternatively, 2-furyl-n-pentylketone may be prepared by way of the hydroacylation of 1-pentene with furfural in the presence of cocatalyst Wilkinson complex and 2-amino-3-picoline.

SUMMARY OF THE INVENTION

The invention comprises a process of making a compound comprising the steps of: reacting a furfural with 1,3-dithiopropane to form a 1,3-dithiane derivative; metalizing the 1,3-dithiane derivative to form a metalodithiane derivative; reacting the metalodithiane derivative with a halide or pseudohalide to form a ketone precursor; and hydrolyzing the ketone precursor to form a furyl ketone.

DETAILED DESCRIPTION OF THE EXAMPLE EMBODIMENTS

The invention relates to process wherein 2-furyl-alkylketones are prepared using lithiodithiane chemistry. Conversion of the carbonyl group into a 1,3-dithiane moiety can offer a stable intermediate that may be lithiated and reacted with various electrophiles to afford the desired extended alkyl chain analogs. The resulting 1,3-dithiane derivative may be hydrolyzed using various conditions to give the preferred carbonyl compound. The products of the process include, but are not limited to, 2-furyl-n-pentyl ketone and analogs of varying alkyl chain length. The process is a three-step sequence in which the first involves the preparation of the 1,3-dithiane derivative of furfural.

The process can allow for the simple preparation of large amounts of material with inexpensive reagents. The process may be preferred to past synthetic methods in that may be applicable to large-scale preparations, including multi-gram quantities, the steps may be easily carried out, and the necessary reagents may be inexpensive. The lithiodithiane synthetic strategy had not been previously used for large-scale synthesis.

In the first step of the process, a furfural is reacted with 1,3-dithiopropane as shown in Eq. (1). $R^1$, $R^2$, and $R^3$ can be hydrogen or any other groups. It is to be understood that in all cases, the mention of a reactant may refer to a single reactant or to a combination or mixture of more than one such reactant. The reaction can be catalyzed with an acid catalyst. Suitable acid catalysts include, but are not limited to, trimethylsilylchloride, Lewis acid, arylsulfonic acid, haloalkylsulfonic acid, boron trifluoride, tetrafluoroboric acid, and acid having normucleophilic conjugate bases.

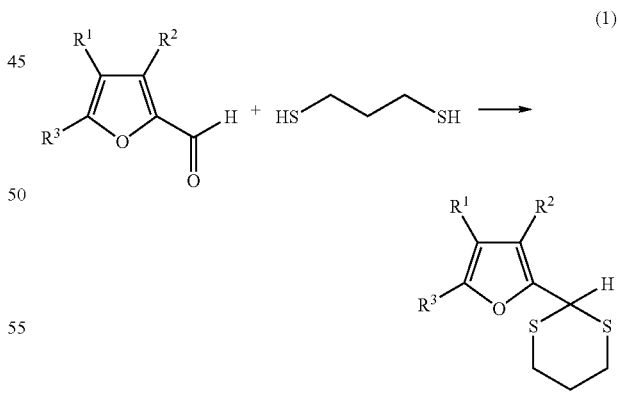

(1)

In the next step, the 1,3-dithiane derivative is metalated. This can be done by reacting the 1,3-dithiane derivative with a metal compound such as a metal hydride, an organolithium compound, or a Grignard reagent. A suitable metal compound is n-butyl lithium, as shown in Eq. (2). Other suitable metal compounds include, but are not limited to, sodium hydride, lithium hydride, lithium aluminum hydride, methyl lithium, phenyl lithium, t-butyl lithium, and s-butyl lithium.

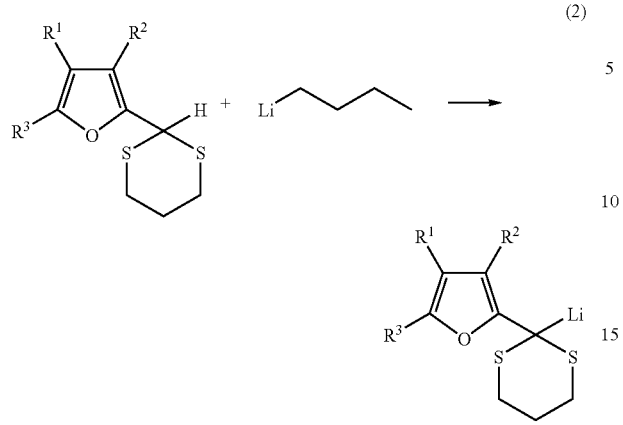

(2)

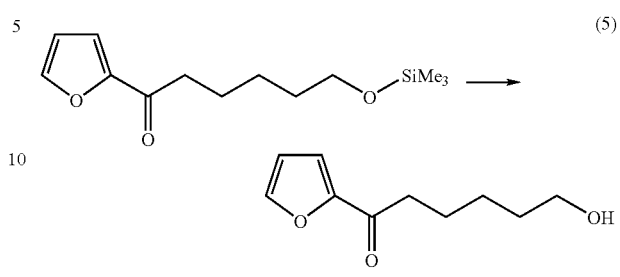

(5)

In the next step, the metalodithiane derivative is reacted with a halide or pseudohalide as shown in Eq. (3). The halide or pseudohalide may comprise an organic residue, R, and a leaving group. Suitable compounds include, but are not limited to, alkylhalides, n-pentyl bromide, n-pentyl iodide, $C_2$–$C_{14}$ alkyl halides, arylsulfonates, fluoroalkylsulfonates, and alkylsulfonates.

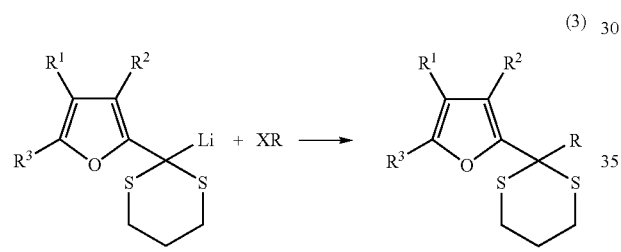

(3)

In the final step, the carbonyl group is regenerated by hydrolyzing the ketone precursor as shown in Eq. (4). Suitable systems for this hydrolysis include, but are not limited to, mercuric oxide and $BF_3OEt_2$; mercuric perchlorate and methanol; copper II chloride, copper oxide, and acetone; dimethylsulfoxide; and dioxane and hydrochloric acid.

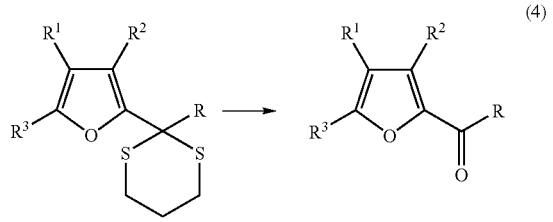

(4)

In some embodiments, an additional step may be performed when the halo- or pseudohalo compound has a protected functional group. This kind of compound can be used when the protected group could react with the furan derivative. In the additional step, the protected group is deprotected. Suitable protected groups include, but are not limited to, ω-hydroxy protected as a silyl ether, ω-carboxy protected as a silyl ester, and ω-amino protected as a methoxymethyl derivative. Eq. (5) shows an example of this step when the protected group is ω-hydroxy.

In one embodiment, a chloroform solution of furfural is cooled to 0° C. and mixed with one equivalent of 1,3-propanedithiol and a catalytic amount of acid catalyst, trimethylsilylchloride. The chilled solution is gradually warmed to RT overnight and the resulting 1,3-dithiane derivative is dissolved in anhydrous THF and reacted with a 2.5 M solution of n-butyl lithium in hexanes at −78° C. to generate the lithiodithiane intermediate. A THF solution of the necessary alkyl halide or alkylpseudohalide is then added and the mixture is slowly warmed to RT overnight. Following work-up, the carbonyl functionality is recovered by hydrolysis of the 1,3-dithiane moiety using two equivalents each of red mercuric (II) oxide and $BF_3OEt_2$ in an aqueous 15% THF solution with vigorous stirring.

Having described the invention, the following examples are given to illustrate specific applications of the invention. These specific examples are not intended to limit the scope of the invention described in this application.

EXAMPLE 1

Preparation of 2-furfuryl-1,3-dithiane—Furfural (40 mL, 0.4825 mol) was dissolved in $CHCl_3$ (400 mL) and cooled to 0° C. (ice bath) with 1,3-propanedithiol (48.5 mL, 0.482 mol, 1 eq) and a catalytic amount of TMSCl (3 pipets full). The reaction mixture was allowed to warm gradually to room temperature overnight and then partitioned with aqueous 5% NaOH (200 mL) and separated. The aqueous layer was extracted with $Et_2O$ and the combined organics were dried ($Na_2SO_4$), filtered, and evaporated to afford crude furfuryl dithiane (85 g, 0.457 mol, 94.8% yield), which was taken on to the next step without further purification. $^1H$ NMR: δ 7.38 (m, 1H), 6.40 (m, 1H), 6.35 (m, 1H), 5.23 (s, 1H, —SH), 2.97 (m, 4H), 2.19–2.10 (m, 1H), 2.05–1.94 (m, 1H). $^{13}C$ NMR: δ 152.2, 142.7, 111.0, 108.3, 42.5, 30.7, 25.7.

EXAMPLE 2

Preparation of 2-furfuryl-n-pentyl-1,3-dithiane—Furfuryl dithiane from Example 1 (40.46 g, 0.217 mol) was dissolved in anhydrous THF (230 mL) and cooled to −78° C. (dry ice/acetone). A solution of n-BuLi (2.5 M/hexanes, 87 mL, 0.218 mol, 1 eq) was added dropwise over 2 hr, and the mixture was allowed to stir 0.5 hr further. A solution of n-pentyl bromide (27 mL, 0.218 mol) in THF (200 mL) was then added dropwise and the reaction mixture was then warmed to RT overnight.

The mixture was cooled to 0° C. (ice bath) and quenched with saturated $NH_4Cl$ (150 mL) and allowed to warm to RT. The resulting mixture was partitioned between $Et_2O$ and H$_2$O then separated. The aqueous layer was extracted with Et$_2$O (2×) and the combined organics were washed with 5% aq. NaHCO$_3$ (2×), H$_2$O, brine, dried (Na$_2$SO$_4$), filtered, and evaporated to afford crude dithiane (62.4 g). The dark residue was passed through a short plug of silica gel and recollected to yield the furfuryl dithiane addition product (53.76 g, 0.211 mol, 97.0% yield), which was taken on to the next step without further purification. $^1$H NMR: δ 7.44 (dd, 1H, $^4J_{H,H}$=1.8 Hz, $^3J_{H,H}$=0.8 Hz, H-2), 6.55 (dd, 1H, $^3J_{H,H}$=3.2 Hz, $^3J_{H,H}$=0.8 Hz, H-3), 6.37 (dd, 1H, $^3J_{H,H}$=3.2Hz, $^4J_{H,H}$=1.8Hz, H-4), 2.90 (m, 2H), 2.71 (m, 2H, 1,3-dithiane), 1.99 (m, 4H), 1.27 (m, 6H, H-8, H-9, H-10), 0.85 (t, 3H, $^3J_{H,H}$=7.0 Hz, H-11). $^{13}$C NMR: δ 154.8, 142.7, 111.0, 110.7, 52.8, 42.8, 32.0, 28.3, 25.8, 24.0, 22.8, 14.4.

EXAMPLE 3

Preparation of 2-furyl-n-pentylketone—BF$_3$OEt$_2$ (51 mL, 0.406 mol, 2 eq) was dissolved in aqueous 15% THF (420 mL) and red Hg(II)O (91.40 g, 0.422 mol, 2 eq) was added with mechanical stirring. A solution of dithiane from Example 2 (53.76 g, 0.211 mol) in THF (190 mL) was added dropwise slowly and the mixture was then allowed to stir overnight. The reaction mixture was then filtered through celite and then treated with saturated NaHCO$_3$ and filtered through celite again rinsing with Et$_2$O. The filtrate was then separated and the organic layer was washed with saturated NaHCO$_3$ (2×), brine, dried (Na$_2$SO$_4$), filtered, and evaporated. The residue was distilled under vacuum (0.2 mm Hg) to yield furyl ketone (R=n-C$_5$H$_{11}$, b.p. 73–74° C., 22.54 g, 0.136 mol, 64.3% yield). $^1$H NMR: δ 7.57 (dd, 1H, $^3J_{H,H}$=1.6 Hz, $^4J_{H,H}$=0.76 Hz, H-2), 7.17 (dd, 1H, $^3J_{H,H}$=3.5 Hz, $^4J_{H,H}$=0.74 Hz, H-4), 6.52 (dd, 1H, $^3J_{H,H}$ 1.6 Hz, $^3J_{H,H}$=3.5 Hz, H-3), 2.80 (t,2H $^3J_{H,H}$=7.4 Hz, H-7), 1.71 (quintet, 2H, $^3J_{H,H}$=7.4 Hz, H-8), 1.33 (m, 4H, H-9, H-10), 0.90 (t, 3H, $^3J_{H,H}$=7.0, H-11). $^{13}$CNMR: δ 190.3, 153.2, 146.6, 117.2, 112.5, 38.9, 31.9, 24.4, 22.9, 14.3.

EXAMPLE 4

Preparation of 2-furyl-n-undecyl-1,3-dithiane—Furfuryl dithiane from Example 1 (5.02 g, 27.0 mmol) was dissolved in anhydrous THF (24 mL) and cooled to −78° C. (dry ice/acetone). A solution of n-BuLi (2.5 M/hexanes, 11.0 mL, 27.5 mmol, 1 eq) was added dropwise and the mixture was allowed to stir 0.5 hr further. A solution of n-undecyl bromide (6.0 mL, 26.8 mmol) in THF (24 mL) was then added dropwise and the reaction mixture was then warmed to RT overnight.

The mixture was cooled to 0° C. (ice bath) and quenched with saturated NH$_4$Cl (50 mL) and allowed to warm to RT. The resulting mixture was partitioned between Et$_2$O and H$_2$O then separated. The aqueous layer was extracted with Et$_2$O (2×) and the combined organics were washed with 5% aq. NaHCO$_3$ (2×), H$_2$O, brine, dried (Na$_2$SO$_4$), filtered, and evaporated to afford crude residue. The dark residue was purified over silica gel eluting with 5% EtOAc/hexane to collect furfuryl dithiane addition product (5.65 g, 16.61 mmol, 62.0% yield), which was taken on to the next step without further purification. $^1$H NMR: δ 7.43 (dd, 1H, $^4J_{H,H}$=1.8 Hz, $^3J_{H,H}$=0.9 Hz, H-2), 6.53 (dd, 1H, $^3J_{H,H}$=3.2 Hz, $^3J_{H,H}$=0.9 Hz, H-3), 6.37 (dd, 1H, $^3J_{H,H}$=1.8Hz, H-4), 2.88 (m, 2H), 2.70 (m, 2H, 1,3-dithiane), 2.06 (m, 4H), 1.30–1.21 (m, 18H), 0.89 (t, 3H, $^3J_{H,H}$=7.0 Hz, H-17). $^{13}$C NMR: δ 154.8, 142.7, 111.0, 110.7, 52.8, 42.9, 32.3, 30.7, 30.1, 30.0, 29.9, 29.8, 29.7, 28.6, 28.3, 25.8, 24.3, 23.1, 14.6.

EXAMPLE 5

Preparation of 2-furyl-n-undecylketone—BF$_3$OEt$_2$ (4.15 mL, 33.0 mmol, 2 eq) was dissolved in aqueous 15% THF (34 mL) and red Hg(II)O (7.22 g, 33.3 mmol, 2 eq) was added with mechanical stirring. A solution of dithiane from Example 4 (5.64 g, 16.6 mmol) in THF (14 mL) was added dropwise slowly and the mixture was then allowed to stir overnight. The reaction mixture was then filtered through celite and then treated with saturated NaHCO$_3$ and filtered through celite again rinsing with Et$_2$O. The filtrate was then separated and the organic layer was washed with saturated NaHCO$_3$ (2×), brine, dried (Na$_2$SO$_4$), filtered, and evaporated to afford furyl ketone (R=n-C$_{11}$H$_{23}$, 2.29 g, 9.13 mmol, 55.1% yield). $^1$H NMR: δ 7.56 (s, 1H, H-2), 7.16 (dd, 1H, $^3J_{H,H}$=3.3 Hz, H-4), 6.51 (dd, 1H, $^3J_{H,H}$=1.6 Hz, $^3J_{H,H}$=3.5 Hz, H-3), 2.80 (t, 2H, $^3J_{H,H}$=7.5 Hz, H-7), 1.70 (quintet, 2H, $^3J_{H,H}$=7.5 Hz, H-8), 1.39–1.20 (m, 16H, H-9-16), 0.86 (t, 3H, $^3J_{H,H}$=6.9, H-17). $^{13}$C NMR: δ 190.3, 146.6, 117.3, 112.5, 38.9, 32.3, 30.0, 29.95, 29.9, 29.85, 29.8, 29.7, 24.8, 23.0, 14.5.

Obviously, many modifications and variations of the present invention are possible in light of the above teachings. It is therefore to be understood that the claimed invention may be practiced otherwise than as specifically described.

What is claimed is:

1. A process of making a compound comprising the steps of:
   reacting a furfural with 1,3-dithiopropane to form a 1,3-dithiane derivative;
   metalizing the 1,3-dithiane derivative to form a metalodithiane derivative;
   reacting the metalodithiane derivative with a halide or psetidohalide selected from alkyl halide, arylsulfonates, fluoroalkylsulfonate and alkylsulfonate to form a ketone precursor; and
   hydrolyzing the ketone precursor to form a furyl ketone.

2. The process of claim 1, wherein the furfural is unsubstituted furfural.

3. The process of claim 1, wherein the step of reacting the furfural with 1,3-dithiopropane is catalyzed with an acid catalyst.

4. The process of claim 3, wherein the acid catalyst is trimethylsilylehioride.

5. The process of claim 3, wherein the acid catalyst is selected from the group consisting of Lewis acids, arylsulfonic acids, haloalkylsulfonic acids, boron trifluoride, tetrafluoroboric acid, and acids having nonnucleophilic conjugate bases.

6. The process of claim 1, wherein the metalating step comprises reacting the 1,3-dithiane derivative with a metal compound selected from the group consisting of metal hydrides, organolithium compounds, and Grignard reagents.

7. The process of claim 6, wherein the metal compound is n-butyl lithium.

8. The process of claim 6, wherein the metal compound is selected from the group consisting of sodium hydride, lithium hydride, lithium aluminum hydride, methyl lithium, phenyl lithium, t-butyl lithium, and s-butyl lithium.

9. The process of claim 1, wherein the halide or pseudohalide is an alkylhalide.

10. The process of claim 9, wherein the alkylhalide is selected from the group consisting of n-pentyl bromide and n-pentyl iodide.

11. The process of claim 9, wherein the alkylhalide is a $C_2$–$C_{14}$ alkyl halide.

12. The process of claim 1, wherein the halide or pseudohalide is selected from the group consisting of arylsulfonates, fluoroalkylsulfonates, and alkylsulfonates.

13. The process of claim 1, wherein the hydrolyzing step comprises reacting with mercuric oxide and $BF_3OEt_2$.

14. The process of claim 1, wherein the hydrolyzing step comprises reacting with a compound or mixture selected from the group consisting of mercuric perchlorate and methanol; copper II chloride, copper oxide, and acetone; dimethylsulfoxide;

and dioxane and hydrochloric acid.

15. The process of claim 1, wherein the halide or pseudohalide has a protected functional group, and further comprising the step of:

deprotecting the protected functional group.

16. The process of claim 15, wherein the protected functional group is selected from the group consisting of ω-hydroxy protected as a silyl ether, ω-carboxy protected as a silyl ester, and ω-amino protected as a methoxymethyl derivative.

17. The process of claim 9, wherein the alkylhalide is n-pentyl bromide.

* * * * *